US011759479B2

(12) United States Patent
Reynolds

(10) Patent No.: US 11,759,479 B2
(45) Date of Patent: Sep. 19, 2023

(54) COMPOSITIONS COMPRISING A MANGANESE MINERAL AND METHODS OF USE

(71) Applicant: Ohm Creations, LLC, Tuscaloosa, AL (US)

(72) Inventor: Ruth Reynolds, Tuscaloosa, AL (US)

(73) Assignee: OHM CREATIONS, LLC, Tuscaloosa, AL (US)

( * ) Notice: Subject to any disclaimer, the term of this patent is extended or adjusted under 35 U.S.C. 154(b) by 410 days.

(21) Appl. No.: 17/221,645

(22) Filed: Apr. 2, 2021

(65) Prior Publication Data
US 2022/0313732 A1   Oct. 6, 2022

(51) Int. Cl.
| | |
|---|---|
| *A61K 33/32* | (2006.01) |
| *A61K 8/02* | (2006.01) |
| *A61K 8/04* | (2006.01) |
| *A61K 8/19* | (2006.01) |
| *A61K 9/00* | (2006.01) |
| *A61K 9/06* | (2006.01) |
| *A61K 9/16* | (2006.01) |
| *A61Q 19/08* | (2006.01) |
| *A61K 38/01* | (2006.01) |

(52) U.S. Cl.
CPC ............ *A61K 33/32* (2013.01); *A61K 8/0225* (2013.01); *A61K 8/042* (2013.01); *A61K 8/19* (2013.01); *A61K 9/0014* (2013.01); *A61K 9/0053* (2013.01); *A61K 9/0073* (2013.01); *A61K 9/06* (2013.01); *A61K 9/16* (2013.01); *A61K 38/014* (2013.01); *A61Q 19/08* (2013.01)

(58) Field of Classification Search
CPC .......... A61K 33/32; A61K 8/042; A61K 8/19; A61K 9/0014; A61K 9/0073; A61K 9/06
See application file for complete search history.

(56) References Cited

U.S. PATENT DOCUMENTS

| | | | | |
|---|---|---|---|---|
| 2006/0246029 | A1* | 11/2006 | Patt .................. | A61Q 19/08 424/70.14 |
| 2007/0187327 | A1* | 8/2007 | George ............... | A61P 17/00 210/639 |
| 2008/0234195 | A1* | 9/2008 | Long .................. | A61K 8/982 514/1.1 |
| 2009/0297628 | A1* | 12/2009 | Launay ............... | A61K 8/19 424/647 |
| 2018/0237498 | A1* | 8/2018 | Alkayali ............. | A61Q 19/00 |

OTHER PUBLICATIONS

Elements—Mineral Bath; 2021 Ohm State of Mind [retrieved on Jul. 22, 2021]. Retrieved from the internet, <URL: https://ohmstateofmind.com/collections/bath/products/elements.html> Jul. 22, 2021.
2 New Bath! Pulse—Micronutrient Vibration Mineral Bath; 2021 Ohm State of Mind [retrieved on Jul. 22, 2021]. Retrieved from the internet: <https://ohmstateofmind.com/collections/bath/products/pulse-micronutrient-vibration-mineral-bathteofmind.com/collections/bath/products/pulse-.html> Jul. 22, 2021.
Simple—Mineral Bath; 2021 Ohm State of Mind, [retrieved on Jul. 22, 2021]. Retrieved from the internet: <https://ohmstateofmind.com/collections/bath/products/simple-holistic-mineral-bath.html> Jul. 22, 2021.
Clean—Detoxifying Mineral Bath; 2021 Ohm State of Mind; [retrieved on Jul. 22, 2021]. Retrieved from the internet: <https://ohmstateofmind.com/collections/bath/products/clean-a-detoxifying-holistic-mineral-bath.html> Jul. 22, 2021.
1 New Bath! Ocean Mineral Bath; 2021 Ohm State of Mind; [retrieved on Jul. 22, 2021]. Retrieved from the internet: <https://ohmstateofmind.com/products/ocean-mineral-bath.html> Jul. 22, 2021.
Dharma + rose quartz libido Topical blend; 2021 Ohm State of Mind; [retrieved on Jul. 22, 2021]. Retrieved from the internet: <https://ohmstateofmind.com/collections/topical-mineral-remedies/products/dharma-rose-quartz.html> Jul. 22, 2021.
Madness—Anxiety & Calm Blend; 2021 Ohm State of Mind; [retrieved on Jul. 22, 2021], Retrieved from the internet: <https://ohmstateofmind.com/collections/topical-mineral-remedies/products/madness.html> Jul. 22, 2021.
Jade Joint and Arthritis Blend; 2021 Ohm State of Mind; [retrieved on Jul. 22, 2021], Retrieved from the internet: <https://ohmstateofmind.com/collections/topical-mineral-remedies/products/jade-%E7%8E%89-joints-arthritis-damage-erosion.html> Jul. 22, 2021.
Revive—Joint Invigoration Blend; 2021 Ohm State of Mind; [retrieved on Jul. 22, 2021]. Retrieved from the internet: <https://ohmstateofmind.com/collections/topical-mineral-remedies/products/revive.html> Jul. 22, 2021.
Mineral Diffusing Blend—Catch & Release Anti-Viral; 2021 Ohm State of Mind; [retrieved on Jul. 22, 2021]. Retrieved from the internet: <https://ohmstateofmind.com/collections/mineral-diffusing-blends/products/catch-release-diffusing-blend.html> Jul. 22, 2021.
Mineral Diffusing Blend—Elements; 2021 Ohm State of Mind; [retrieved on Jul. 22, 2021]. Retrieved from the internet: <https://ohmstateofmind.com/collections/mineral-diffusing-blends/products/elements-diffusing-blend.html> Jul. 22, 2021.
K-9 Madness—Anxiety Remedy; 2021 Ohm State of Mind; [retrieved on Jul. 22, 2021]. Retrieved from the internet: <https://ohmstateofmind.com/collections/k-9/products/k-9-madness.html> Jul. 22, 2021.

(Continued)

*Primary Examiner* — Mina Haghighatian
(74) *Attorney, Agent, or Firm* — Nicholas J. Landau; Maynard Nexsen PC

(57) ABSTRACT

Compositions comprising a manganese mineral are provided. In specific embodiments, the manganese mineral contains manganese carbonate ($MnCO_3$), which may be in the form of rhodochrosite. The compositions may be administered topically to a subject, or in some versions by inhalation. For example, the compositions may be administered by direct contact with the subject's skin or by inhalation through the subject's nasal passages or mouth. Such application of the disclosed compositions may increase the subject's collagen synthesis, prolidase activity (an enzyme responsible for collagen function), and manganese superoxide dismutase activity (an antioxidant having manganese in its active site) in the subject.

11 Claims, No Drawings

(56) References Cited

OTHER PUBLICATIONS

K-9 Revive Invigorating Joint Blend; 2021 Ohm State of Mind; [retrieved on Jul. 22, 2021]. Retrieved from the internet: <https://ohmstateofmind.com/collections/k-9/products/k-9-revive.html> Jul. 22, 2021.

Stillness Meditation Minerals; 2021 Ohm State of Mind; [retrieved on Jul. 22, 2021]. Retrieved from the internet: <https://ohmstateofmind.com/collections/holistic-meditation-minerals/products/stillness.html> Jul. 22, 2021.

\* cited by examiner

COMPOSITIONS COMPRISING A MANGANESE MINERAL AND METHODS OF USE

I. DEFINITIONS

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terminology used herein is for the purpose of describing particular embodiments only and is not intended to be limiting. As used herein, the singular forms "a," "an," and "the" are intended to include the plural forms as well, unless the context clearly indicates otherwise.

The terms "first," "second," and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. For biological systems, the term "about" refers to an acceptable standard deviation of error, preferably not more than 2-fold of a given value. Numerical quantities given herein are approximate unless stated otherwise, meaning that the term "about" or "approximately" can be inferred when not expressly stated.

All methods described herein can be performed in any suitable order unless otherwise indicated herein or otherwise clearly contradicted by context. The use of any and all examples, or exemplary language (e.g., "for example" and "such as") provided herein, is intended merely to better illuminate the invention and does not pose a limitation on the scope of the invention unless otherwise claimed. No language in the specification should be construed as indicating any non-claimed element as essential to the practice of the invention. Terms such as "at least one of A and B" should be understood to mean "only A, only B, or both A and B." The same construction should be applied to longer lists (e.g., "at least one of A, B, and C").

The terms "prevention," "prevent," "preventing," "suppression," "suppress," and "suppressing" as used herein refers to a course of action (such as implanting a medical device) initiated prior to the onset of a clinical manifestation of a disease state or condition so as to prevent or reduce such clinical manifestation of the disease state or condition. Such preventing and suppressing need not be absolute to be useful.

The terms "treatment," "treat," and "treating" as used herein refers to a course of action (such as administering a disclosed composition) initiated after the onset of a clinical manifestation of a disease state, condition, or symptom so as to eliminate or reduce such clinical manifestation of the disease state, condition, or symptom. Such treating need not be absolute to be useful.

The phrase "in need of" supplementing or increasing a biological activity as used herein refers to a judgment made by a caregiver that a patient requires or will benefit from supplementation of the activity. This judgment is made based on a variety of factors that are in the realm of a caregiver's expertise, but that includes the knowledge that the patient is ill, or will be ill, as the result of a condition that is treatable or preventable by a composition or method of the present disclosure.

As used herein, terms such as "administering" or "administration" include acts such as prescribing, dispensing, giving, or taking a substance (such as the disclosed compositions), such that what is prescribed, dispensed, given, or taken actually contacts the patient's body externally or internally (or both). In embodiments of this disclosure, terms such as "administering" or "administration" include self-administering, self-administration, and the like, of a substance. Indeed, it is specifically contemplated that instructions or a prescription by a medical professional to a subject or patient to take or otherwise self-administer a substance is an act of administration. It is also specifically contemplated that providing labeling instructions to a subject or patient to take or otherwise self-administer a substance is an act of administration.

The terms "increase," "enhance," "stimulate," "supplement," and "induce" (and like terms) generally refer to the act of improving or increasing, either directly or indirectly, a function, behavior, or activity relative to the natural, expected, or average relative to current conditions.

The term "individual," "subject," or "patient" as used herein refers to any animal, including mammals, such as mice, rats, other rodents, rabbits, canines, cats, swine, cattle, sheep, horses, or primates, and humans. The term may specify male or female or both, or exclude male or female.

The terms "therapeutically effective" or "effective" may be used interchangeably and refer to an amount of a disclosed composition, e.g., one comprising a manganese mineral. For example, a therapeutically effective amount of a composition comprising a manganese mineral in a predetermined amount calculated to achieve the desired effect, i.e., to effectively supplement collagen synthesis, prolidase activity, and/or manganese superoxide dismutase activity.

The term "synthesis" or similar terms refer to the formation or building of a larger substance or compound, such as a protein, from smaller compounds, such as amino acids. For example, collagen synthesis refers to the production of the protein collagen in the body from free building blocks, such as glycine, proline, and hydroxyproline. Collagen synthesis may involve any number of steps, precursors, enzymes, and cofactors. An increase in collagen synthesis results in an increase in the amount of collagen in the body (e.g., in the blood, tissue, etc.). Collagen has a long half-life in the body, and collagen synthesis can occur in conjunction with the degradation of existing collagen, which is sometimes termed "collagen recycling."

II. COMPOSITIONS

Manganese is a trace mineral and is considered an essential nutrient that the human body cannot produce, but it can store it in the liver, pancreas, bones, kidneys, and brain. Manganese is essential for numerous bodily functions, including the metabolism of amino acids, cholesterol, glucose, and carbohydrates. It also helps the body form connective tissue, bones, blood clotting factors, and sex hormones, and plays a role in calcium absorption, blood sugar regulation, and reducing inflammation. Manganese is also necessary for normal brain and nerve function.

The present disclosure provides for compositions containing a manganese mineral. In this context "mineral" refers to a naturally occurring inorganic element or compound having an orderly internal structure and characteristic chemical composition, crystal form, and physical properties. It has been found that manganese can have numerous beneficial uses. It can be used to address cosmetic concerns, such as improving the appearance of the skin; as well as medical concerns, such as preventing or treating diseases caused by oxidative stress, including neurodegenerative diseases, cancer, and inflammatory disorders; and medical concerns related to disorders of the connective tissue and the bones.

Without wishing to be bound by any hypothetical model, the aforementioned benefits of manganese are believed to be due to manganese's role as a coenzyme in several biological processes, including collagen synthesis and free radical defense systems. Supplemental collagen is generally provided in the form of hydrolyzed collagen, also referred to as "collagen peptides." Manganese is a cofactor of prolidase. Prolidase plays an important role in the recycling of proline for collagen synthesis and cell growth and probably serves as an interface between protein nutrition and matrix breakdown. Prolidase activity may be a limiting factor in the regulation of collagen synthesis. It is believed that prolidase plays an important role in making collagen peptides (e.g., hydrolyzed collagen) available for collagen synthesis after ingestion. Manganese is also a component of the antioxidant manganese superoxide dismutase (MnSOD), which helps fight free radicals. Accordingly, compositions comprising a manganese mineral find use in, for example, supporting collagen synthesis and the body's ability to fight oxidative stress (discussed further in Section III, below).

The manganese mineral comprises the element manganese. There are at least 470 species of minerals containing manganese. Examples of such minerals include, but are not limited to, rhodochrosite, rhodonite, bixbyite, pyrolusite, and bahariyaite. The manganese mineral may be obtained from a natural source or synthetically produced. For example, in a specific embodiment, the manganese mineral comprises manganese carbonate ($MnCO_3$). Manganese carbonate occurs naturally as the mineral rhodochrosite, but is oftentimes produced synthetically. Some embodiments of the manganese mineral are water insoluble.

The manganese mineral may be undyed and/or untreated. In some embodiments, the manganese mineral may be substantially free of impurities. It is believed that using undyed, untreated, and/or substantially pure manganese mineral will lessen the risk of unwanted side effects as well as increase the probability of producing desired cosmetic and medical outcomes.

In some embodiments, the manganese mineral is in the form of a powder. The powder may be produced by pulverizing or grinding the manganese mineral. For example, the manganese mineral may be pulverized or ground into any particle size. Exemplary particle sizes range from about 50 μm to about 200 μm. In specific embodiments, the particle sizes range from about 75 μm to about 150 μm.

The powder may be comprised of various particle size distributions of the manganese mineral. For example, in some embodiments, the powder comprises at least about 50% of manganese mineral particles that are less than about 150 μm in size. In some embodiments, the powder comprises at least about 50% of manganese mineral particles that are at least about 75 μm to about 150 μm in size. In further embodiments, the powder comprises at least about 75% of manganese mineral particles that are at least about 75 μm to about 150 μm in size. In still further embodiments, the powder comprises at least about 80, 85, 90, or 95% of manganese mineral particles that are at least about 75 μm to about 150 μm in size.

The compositions of the disclosure may be used in the methods of use of the present disclosure. Such compositions are administered to a subject in amounts sufficient to deliver a therapeutically effective amount of the manganese mineral so as to be effective in the methods disclosed herein. The therapeutically effective amount may vary according to a variety of factors such as, but not limited to, the subject's condition, weight, sex and age.

The compositions may be formulated to be provided to the subject topically. Topical compositions may be designed for cutaneous administration and/or inhalational administration, as it is believed that the manganese mineral can be effective when exposed to the upper respiratory tract.

In embodiments wherein the compositions are designed for inhalational administration, the disclosed compositions are formulated to be inhaled through the subject's mouth or nasal passages. The composition should be suitable and safe for inhalation. In such embodiments, the compositions may comprise a suspension of the manganese mineral in a fluid carrier, including but not limited to, viscous water or saline. In said embodiments, the fluid carrier and the manganese mineral should be safe for inhalation. For example, both the carrier and the manganese mineral should be of sufficient purity as to be suitable for inhalation.

In embodiments wherein the compositions are designed for cutaneous administration, the disclosed compositions are formulated for direct contract with a portion of the subject's body, such as the face, trunk, arms, or legs. For example, the topical compositions may be applied (e.g., rubbed) onto a portion of a subject's body, and/or a portion of the subject's body may be submerged in the composition. In some embodiments, the topical compositions are applied to a patch, bandage, or dressing for transdermal delivery or delivery directly to a particular site.

The topical compositions may be dry powdered preparations of the manganese mineral. Such compositions may be formulated to be applied directly, such as through rubbing, onto the skin of a subject. Advantageously, a dry powdered preparation may act as a physical exfoliant for the skin and remove dead skin cells from the surface of the subject's skin.

In some embodiments, the topical compositions comprise a suspension of the manganese mineral in a carrier, as mentioned above. For example, the compositions may take various forms, such as but not be limited to, aqueous mineral mixtures, aqueous mineral suspensions, ointments, creams, pastes, and emulsions. Such compositions can be admixed with a variety of carrier materials well known in the art, such as, water, saline, alcohols, aloe vera gel, allantoin, glycerine, vitamin A and E oils, mineral oil, PPG2 myristyl propionate, and the like, to form alcoholic solutions, oils, topical cleansers, cleansing creams, skin gels, skin lotions, shampoos, and hydrosols.

The compositions may further comprise any suitable additive that has been used in cosmetics or other skin care compositions. These include, but are not limited to aloe vera, antioxidants, azulene, beeswax, benzoic acid, beta-carotene, butyl stearate, camphor, castor oil, chamomile, cinnamate, clay, cocoa butter, coconut oil, cucumber, dihydroxyacetone (DHA), elastin, estrogen, *ginseng*, gluramic acid, glycerin, glycolic acid, humectant, hydroquinone, lanolin, lemon, liposomes, mineral oil, monobenzone, nucleic acids, oatmeal, paba, panthenol, petroleum jelly, propelene glycol, royal jelly, seaweed, silica, sodium lauryl sulfate sulfur, witch hazel, zinc, zinc oxide, copper, hyaluronic acid and shea butter. Additives which aid in improving the elasticity of tissues such as retinoic acid, tretinoin, vitamin E, sources of copper, magnesium ions, retinol, copper peptides, and any one of the 20 standard amino acids may also be added to the compositions of the present invention. Inclusion of a skin exfoliant or dermal abrasive preparation may also be used.

The compositions of the present disclosure may further comprise agents which improve the solubility, half-life, absorption, etc. of the manganese mineral. Furthermore, the compositions of the present disclosure may further comprise agents that attenuate undesirable side effects and/or decrease the toxicity of the manganese mineral. Examples of such agents are described in a variety of texts, such as, but not limited to, Remington: The Science and Practice of Pharmacy (20$^{th}$ Ed., Lippincott, Williams & Wilkins, Daniel Limmer, editor).

The compositions of the present disclosure may be formulated to be administered only once to the subject or more than once to the subject. Furthermore, when the compositions are administered to the subject more than once, a variety of regimens may be used, such as, but not limited to, once per day, once per week, once per month or once per year. The compositions may also be formulated to be administered to the subject more than one time per day. The therapeutically effective amount of the manganese mineral and appropriate dosing regimens may be identified by routine testing in order to obtain optimal activity, while minimizing any potential side effects. In addition, formulation for co-administration or sequential administration of other agents may be desirable.

III. METHODS OF USE

The disclosed compositions can be used, for example, to address concerns associated with decreased collagen synthesis, low prolidase activity, low MnSOD activity, and/or oxidative stress. As humans and animals age, there is an increase in oxidative stress and a decrease in collagen levels, which can cause a myriad of detrimental cosmetic and medical conditions (including but not limited to those involving connective tissues and bone). However, it is believed that manganese may support human health issues when challenged with increased oxidative stress and decreased collagen synthesis.

Thus, the disclosed compositions containing a manganese mineral find use in methods directed towards increasing the synthesis of collagen, the activity of prolidase (the enzyme responsible for collagen function), and the activity of manganese superoxide dismutase (an antioxidant having manganese in its active site) in a subject. Each of these methods is discussed further below:

A. Methods of Increasing Collagen and/or Prolidase Activity

Turning first to collagen synthesis, animals synthesize collagen naturally. Collagen is a group of proteins found in the integument and connective tissues of animals, making up about one third of the whole-body protein content. Many types of collagen are known, with the most common being collagen I (integument, tendon, vascular ligature, organs, the main component of the organic part of bone), collagen II (main component of cartilage), collagen III (main component of reticulate fibers and commonly found alongside type I), collagen IV (forming the bases of cell basement membrane), and collagen V (cell surfaces, hair and placenta). Thus, collagen is essential in maintaining tissue and cartilage structure and integrity.

However, as humans age, collagen synthesis slows down. Collagen makes up 80% of skin and maintains skin elasticity. Collagen in the skin is lost with age. After about the age of 30 humans lose about 1 percent of skin collagen each year. During the five years following menopause about 30% of collagen is lost. As a result, the structural integrity of the skin declines, wrinkles form, and joint cartilage weakens. Consequently, many people turn to collagen supplements, which are readily available in the form of tablets, capsules, and powders. Consuming collagen may have a variety of benefits, from relieving joint pain to improving skin health. Specifically, it is believed that collagen supplements (containing whole or hydrolyzed collagen) may improve the look and overall health of skin, restore or prevent deterioration of the cartilage in joints, increase muscle mass, prevent bone loss, and support a healthy cardiovascular system.

Prolidase is critical for collagen synthesis and degradation. Manganese is a cofactor of prolidase and, thus, is required for the enzyme's activation. Therefore, it is believed that the manganese mineral-containing compositions of the present disclosure would increase a subject's prolidase activity and, thus, stimulate the subject's collagen synthesis, particularly when the subject is taking supplemental collagen. Supplemental collagen is generally provided in the form of hydrolyzed collagen, also referred to as "collagen peptides." Prolidase plays an important role in the recycling of proline for collagen synthesis and cell growth and probably serves as an interface between protein nutrition and matrix breakdown. Prolidase activity may be a step limiting factor in the regulation of collagen synthesis.

In one embodiment, the present disclosure provides for a method of supplementing the activity of prolidase in a subject, the method comprising administering any of the compositions disclosed above topically to the subject. The disclosed compositions may be topically administered by inhalation or by direct contact with the skin. It is believed that administration of the compositions would lead to an increase in prolidase activity. Specifically, the administration of a disclosed composition may lead to a higher level of prolidase activity as compared to a level of prolidase activity prior to administration of the composition. It is believed that an increase in prolidase activity or concentration of free prolidase in the bloodstream would lead to an increase in collagen synthesis.

The method will often further include identifying a subject in need of supplementing prolidase activity, such as a subject identified as, or suspected of, having low prolidase activity. In some embodiments, the subject suffers from one or more of: wrinkles, hair loss, eyelash thinning, slow nail growth, elastosis, joint pain, fatigue, Raynaud's syndrome, fibromyalgia.

In one embodiment, the present disclosure provides for a method of supplementing collagen synthesis in a subject, the method comprising administering any of the compositions disclosed above topically to a subject receiving collagen therapy in an amount effective to increase the synthesis of collagen in the subject. In a preferred embodiment the collagen therapy is hydrolyzed collagen therapy. The disclosed compositions may be topically administered by inhalation or by direct contact with the skin. As discussed above, administration of the disclosed compositions may result in an increased level of manganese in the subject, which will in turn increase the subject's prolidase activity, which is the enzyme responsible for collagen function. Therefore, the administrations of collagen therapy and disclosed compositions may lead to a higher level of collagen synthesis as compared to a level of collagen synthesis prior to administrations of the collagen therapy and disclosed compositions.

The method will often further include identifying a subject in need of supplementing collagen synthesis, such as a subject identified as, or suspected of, having low collagen synthesis. In some embodiments, the subject suffers from one or more of: wrinkles, hair loss, eyelash thinning, slow nail growth, elastosis, joint pain, fatigue, Raynaud's syndrome, fibromyalgia. In further embodiments, the composition containing manganese mineral is administered in an amount effective to improve said one or more of: wrinkles, hair loss, eyelash thinning, slow nail growth, elastosis, joint pain, fatigue, Raynaud's syndrome, fibromyalgia.

The step of administering collagen therapy may comprise administering a supplement to the subject, wherein the supplement is formulated to increase or support the subject's collagen level. In a specific embodiment, the collagen therapy may by orally administered. For example, the collagen therapy may comprise administration of an oral collagen supplement. In such embodiments, the collagen supplement may be sourced from animals, such as pigs, cows, and fish. The composition of the collagen supplement may vary. For example, the collagen supplement may comprise collagen types I, II, III, IV, V, or combinations thereof. In a preferred embodiment the collagen therapy is hydrolyzed collagen therapy.

The collagen therapy and the disclosed compositions may be administered separately, but simultaneously, or in alternation. In some embodiments, the subject can be administered the collagen therapy less than 1 hour, 1, 2, 3, 4, 5, 6, or more hours, or less than 1 day, 1, 2, 3, 4, 5, 6, 7, or more days before administration of the disclosed compositions, and vice versa.

The collagen therapy and/or the compositions of the present disclosure may be administered only once to the subject or more than once to the subject. Furthermore, when the collagen therapy and/or the compositions are administered to the subject more than once, a variety of regimens may be used, such as, but not limited to, once per day, once per week, once per month, or once per year. The collagen therapy and/or the compositions may also be formulated to be administered to the subject more than one time per day.

Advantageously, the aforementioned methods of supplementing the activity of prolidase or collagen in a subject may lead to increased collagen synthesis or the support of undiminished collagen synthesis. Increased collagen synthesis can prevent or treat diseases or symptoms associated with low collagen synthesis, including maintaining or restoring the look and overall health of skin, restoring or preventing deterioration of the cartilage in joints, increasing muscle mass, preventing bone loss, and supporting a healthy cardiovascular system.

B. Method of Increasing Manganese Superoxide Dismutase Activity

It is believed that manganese plays a role in reducing oxidative stress. Oxidative stress is an imbalance of free radicals and antioxidants in the body, which can lead to cell and tissue damage. A large body of scientific evidence suggests that long-term oxidative stress damages the body's cells, proteins, and DNA, which in turn contributes to the development of a number of conditions. Such conditions include, for example, neurodegenerative disorders, cancer, diabetes, asthma, chronic fatigue syndrome, and heart disease, among others.

Manganese is a component of the antioxidant manganese superoxide dismutase (MnSOD), which helps fight free radicals. Antioxidants, such as MnSOD, can help neutralize free radicals and reduce or even help prevent some of the resulting damage. Accordingly, low levels of MnSOD are observed in many diseases, including those associated with oxidative stress (see recitation above). Since MnSOD contains manganese in its active site, manganese availability can impact MnSOD activity. Therefore, it is believed that the manganese mineral-containing compositions of the present disclosure would supplement the activity of manganese superoxide dismutase in a subject.

In one embodiment, the present disclosure provides for a method of supplementing the activity of manganese superoxide dismutase in a subject, the method comprising administering any of the compositions disclosed above topically to the subject. The disclosed compositions may be topically administered by inhalation or by direct contact with the skin. As detailed earlier herein, administration of the disclosed compositions may result in an increased level of manganese in the subject. Because manganese availability impacts the level of MnSOD activity, it is believed that administration of the compositions would lead to an increase in MnSOD activity.

The method will often further include identifying a subject in need of supplementing MnSOD activity, such as a subject identified as, or suspected of, having low MnSOD activity. In some embodiments, the subject suffers from one or more of: fibromyalgia, restless leg syndrome, Parkinson's disease, rosacea, lupus, hypertension, osteoarthritis, and an autoimmune disorder.

In a further embodiment of the method the manganese mineral-containing composition is administered in an amount effective to improve said one or more of: fibromyalgia, restless leg syndrome, Parkinson's disease, rosacea, lupus, hypertension, osteoarthritis, and an autoimmune disorder.

Advantageously, the aforementioned methods of supplementing MnSOD activity in a subject may lead to a reduction of oxidative stress. Reduced oxidative stress prevents or treats diseases or disease conditions associated with oxidative stress, including, for example, neurodegenerative disorders, cancer, diabetes, asthma, chronic fatigue syndrome, and heart disease.

C. Method Steps Applicable to all Methods Disclosed Herein

In any of the methods disclosed herein, when the compositions are applied via a cutaneous route, the disclosed compositions may be applied directly to a portion of the skin of the subject. For example, the disclosed compositions may be applied directly, such as through rubbing onto the face, trunk, arms, or legs of the subject. In such embodiments, the administration may be easily confined to a particular portion of the body on which application of the composition is desired.

In some embodiments, the subject may be at least partially immersed in the disclosed compositions. Such embodiments find particular use with compositions comprising a manganese mineral in a fluid carrier, such as water. For example, the composition may be administered in a reservoir for holding a liquid, such as a bath, a spa tub, a garden tub, a hot tub, a swimming pool, a hydrotherapy tank, a hydrotherapy bath, and a hydrotherapy pool. Advantageously, administration of the compositions in a tub, pool, spa, etc. may offer additional benefits, such as mental and physical relaxation.

When the disclosed compositions are applied via an inhalational route, the disclosed compositions may be administered in an aerosol. An aerosol is a suspension of fine solid particles or liquid droplets in air or another gas. The disclosed compositions may be administered as an aerosol via a diffuser, humidifier, or water mist system. Such embodiments find particular use with compositions comprising a manganese mineral in a fluid carrier, such as water. A benefit of aerosol administration is the convenience of the route. Taking a diffuser as an example, the subject may easily complete other activities while breathing in the disclosed compositions from a nearby diffuser.

In any of the methods disclosed herein, the method may comprise determining an amount of the manganese mineral in the disclosed compositions sufficient to prevent, treat, or supplement one of: low MnSOD activity, low collagen synthesis, low prolidase activity, and combinations thereof (i.e., determining a therapeutically effective amount). Too little of the manganese mineral would fail to provide an effect. On the other hand, excessive manganese mineral could lead to undesired side-effects.

The therapeutically effective amount may vary according to a variety of factors, such as the subject's condition, weight, sex, and age. For example, some embodiments of the method comprise administration of up to the median lethal dose ($LD_{50}$) of an amount of manganese mineral. The $LD_{50}$ can be ascertained using standard toxicological methods, or by reference to past studies.

In some embodiments of the methods disclosed herein, the effect of the disclosed compositions on a subject is compared to a control. For example, the effect of the disclosed compositions on a particular symptom or physiologic indicator can be compared to an untreated subject, or the condition of the subject prior to administration of the disclosed methods. In some embodiments, the symptom or physiologic indicator is measured in a subject prior to administration, and again one or more times after administration is initiated. In some embodiments, the control is a reference level or an average determined from measuring the symptom or physiologic indicator in one or more subjects that do not have the symptom or physiologic indicator to be treated (for example, healthy subjects). In some embodiments, the effect of the administration is compared to a conventional administration that is known in the art.

In any of the disclosed methods herein, the compositions of the present disclosure may be administered only once to the subject or more than once to the subject. Furthermore, when the compositions are administered to the subject more than once, a variety of regimens may be used, such as, but not limited to, once per day, once per week, once per month, or once per year. The compositions may also be formulated to be administered to the subject more than one time per day.

The disclosed compositions can be administered to the subject in combination or alternation with other therapies and therapeutic agents. In some embodiments, the disclosed compositions and the additional therapeutic agent are administered separately, but simultaneously, or in alternation. The disclosed compositions and the additional therapeutic agent can also be administered as part of the same composition. In other embodiments, the disclosed compositions and the second therapeutic agent are administered separately and at different times, but as part of the same treatment regime.

The subject can be administered a first therapeutic agent less than 1, 1, 2, 3, 4, 5, 6, or more hours, or less than 1, 1, 2, 3, 4, 5, 6, 7, or more days before administration of a second therapeutic agent. In some embodiments, the subject can be administered one or more doses of the first agent every 1, 2, 3, 4, 5, 6, 7, 14, 21, 28, 35, or 48 days prior to a first administration of the second agent. The disclosed compositions can be the first or the second therapeutic agent.

The disclosed compositions and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen. Again, the disclosed compositions can be the first or the second therapeutic agent.

Exemplary molecules that may be administered with the disclosed compositions include, but are not limited to, immunotherapeutics, enzymes, antimicrobials, antibiotics, antifungals, antivirals, growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, and pain relievers.

The additional therapeutic agents may be selected based on the condition to be treated. For example, the disclosed compositions can be co-administered with one or more additional agents that function to enhance or promote one or more of collagen synthesis, prolidase activity, and MnSOD activity.

If, after the administration of the disclosed compositions and, optionally, any additional therapeutic agents, the subject still has one or more of low collagen synthesis, low prolidase activity, and low MnSOD activity, or is at risk for the same, then an optional step of the method is to continue administration of the disclosed compositions and/or any additional therapeutic agents.

IV. WORKING EXAMPLES

Example 1. A 57-year-old female took a bovine collagen peptide supplement daily for three months to treat hair loss and skin elasticity. During the three months, this individual reported no visible improvement in skin elasticity or hair loss. At approximately the three-month mark, and in addition to a daily bovine collagen peptide supplement, the individual began using (1) a composition containing rhodochrosite in a bath four to five times a week, and (2) a gel composition containing rhodochrosite three to four times a week. While undergoing this regimen, the individual reported faster nail growth within two weeks, and faster head hair growth (approximately 0.5 inch of new growth) within three weeks. Finally, the individual reported an overall increase in energy level.

Example 2. A 35-year-old female took a bovine collagen peptide supplement daily for one year for knee and hip pain without results. At approximately the one-year mark, and in addition to a daily bovine collagen peptide supplement, the individual began using a composition containing rhodochrosite in the bath four to five times a week. While undergoing this regimen, the individual reported a significant improvement in knee pain after one month, and a significant improvement in hip pain after two months. Finally, the individual reported an overall increase in energy level.

Example 3. A 73-year-old female used various compositions containing rhodochrosite in the bath for two years. At approximately the two-year mark, and in addition to continued use of the compositions, this individual began taking a daily bovine collagen peptide supplement. While undergoing this regimen, the individual reported (1) a decrease in visible forehead wrinkles and faster nail growth within ten days, (2) new eyelash growth within three weeks, and (3) a decrease in visible facial wrinkles within four weeks.

Example 4. A 57-year-old female diagnosed with Raynaud's syndrome used a gel composition containing rhodochrosite daily on her entire body. While undergoing this regimen, the individual reported a decrease in finger pain and joint pain within two weeks. Further, this individual reported that she would apply the gel after strenuous exercise and would notice an immediate relief in fatigue and pain. Finally, the individual reported an overall increase in energy level.

Example 5. A 55-year-old female used (1) various compositions containing rhodochrosite in the bath three to four times a week for two years, and (2) a gel composition containing rhodochrosite four to five times per week for two years. At approximately the two-year mark, and in addition to continued use of the rhodochrosite compositions, this individual began taking a daily bovine collagen peptide supplement for hip and joint pain and skin elasticity. While undergoing this regimen, the individual reported (1) new eyelash growth within two weeks, (2) improved skin elasticity within three weeks, and (3) improvement in hip and joint pain within four weeks.

Example 6. A 47-year-old female diagnosed with fibromyalgia used a composition containing rhodochrosite in the bath and a gel composition containing rhodochrosite daily. At approximately the two-week mark, and in addition to continued use of the rhodochrosite compositions, this individual began taking a daily collagen peptide supplement. While undergoing this regimen, the individual reported a reduction in pain within two weeks, and an overall increase in energy level.

Example 7. A 66-year-old female diagnosed with Restless Leg Syndrome (RLS) used a gel composition containing rhodochrosite on her legs whenever she experienced RLS-related symptoms. This individual reported an immediate cease in symptoms upon application of the gel.

Example 8. A 57-year-old female diagnosed with rosacea used a gel composition containing rhodochrosite daily on her face. After two days of using the gel, this individual reported that all of her facial rosacea symptoms were cleared.

Example 9. A 47-year-old female diagnosed with hypertension used a gel composition containing rhodochrosite on her entire body four to five days a week. This individual reported a noticeable improvement in hypertension.

Example 10. A 70-year-old female diagnosed with osteoarthritis of the hands rubbed a composition containing rhodochrosite powder directly onto her finger joints twice a day. Within three weeks, this individual reported a decrease in joint pain, a reduction in knuckle size, and a noticeable straightening in an afflicted finger.

Example 11. A 66-year-old male had been diagnosed with Parkinson's Disease for six years when he began using a gel composition containing rhodochrosite daily on his entire body. He previously reported lost balance and greatly reduced mobility. However, after three weeks of using the gel, he reported improved energy levels and restoration of balance. Within five weeks, he reported that the redness in his legs had reduced and that his legs began growing hair. This individual has reported further improvements over the course of two years, including resuming exercise (approximately 90 minutes of activity) and teaching college courses.

V. EXEMPLARY EMBODIMENTS

The following are non-limiting examples of specific embodiments of the subject matter disclosed above. This disclosure specifically but non-exclusively supports claims to these embodiments:

Embodiment 1. A method of supplementing collagen synthesis in a subject, the method comprising: administering a composition containing a manganese mineral topically or by inhalation to the subject while the subject is undergoing collagen therapy in an amount effective to increase the synthesis of collagen in the subject.

Embodiment 2. A method of supplementing the activity of manganese superoxide dismutase in a subject, the method comprising: administering a composition containing a manganese mineral topically or by inhalation to the subject.

Embodiment 3. A method of supplementing the activity of prolidase in a subject, the method comprising: administering a composition containing a manganese mineral topically or by inhalation to the subject.

Embodiment 4. A method of treating or preventing a condition associated with low prolidase activity in a subject in need thereof, the method comprising: administering a manganese mineral topically or by inhalation to the subject in an amount effective to treat or prevent the condition associated with low prolidase activity.

Embodiment 5. A method of treating or preventing a condition associated with low manganese superoxide dismutase (MnSOD) in a subject in need thereof, the method comprising: administering a manganese mineral topically or by inhalation to the subject in an amount effective to treat or prevent the condition associated with low MnSOD activity.

Embodiment 6. The method of any one of embodiments 1-5, wherein the manganese mineral contains $MnCO_3$.

Embodiment 7. The method of any one of embodiments 1-5, wherein the manganese mineral is rhodochrosite.

Embodiment 8. The method of any one of embodiments 1-5, wherein the manganese mineral is in the form of a powder.

Embodiment 9. The method of any one of embodiments 1-5, wherein the manganese mineral is in the form of a powder, and wherein at least 50% of the powder is less than about 150 μm in particle size.

Embodiment 10. The method of any one of embodiments 1-5, wherein the manganese mineral is in the form of a powder, and wherein at least 50% of the powder is from 75-150 μm in particle size.

Embodiment 11. The method of any one of embodiments 1-5, wherein the manganese mineral is insoluble in water.

Embodiment 12. The method of any one of embodiments 1-5, wherein the collagen therapy is orally administered.

Embodiment 13. The method of any one of embodiments 1-5, wherein the collagen therapy is administered as hydrolyzed collagen.

Embodiment 14. The method of any one of embodiments 1-5, wherein the composition is a dry powdered preparation of the manganese mineral.

Embodiment 15. The method of any one of embodiments 1-5, wherein the composition is a suspension of the manganese mineral in a fluid carrier.

Embodiment 16. The method of any one of embodiments 1-5, wherein the composition is a suspension of the manganese mineral in water, administered by immersion of the subject in the composition.

Embodiment 17. The method of any one of embodiments 1-5, wherein the composition is a suspension of the manganese mineral in water, administered in at least one of: a bath, a spa tub, a garden tub, a hot tub, a swimming pool, a hydrotherapy tank, a hydrotherapy bath, and a hydrotherapy pool.

Embodiment 18. The method of any one of embodiments 1-5, wherein the composition is administered in the form of one or more of: a gel, a lotion, an oil, viscus water, and a hydrosol.

Embodiment 19. The method of any one of embodiments 1-5, wherein the composition is administered in the form of an aerosol comprising a liquid carrier and the manganese mineral.

Embodiment 20. The method of any one of embodiments 1-5, wherein the subject is suffering from a health or cosmetic condition symptomatic of at least one of: low collagen synthesis, low prolidase activity, and low manganese superoxide dismutase activity.

Embodiment 21. The method of any one of embodiments 1-5, wherein the subject is suffering from one or more of: facial wrinkles, hair loss, eyelash thinning, slow nail growth, elastosis, joint pain, fatigue, Raynaud's syndrome, fibromyalgia, restless leg syndrome, Parkinson's disease, rosacea, lupus, hypertension, and osteoarthritis.

Embodiment 22. The method of any one of embodiments 1-5, wherein the subject is human.

Embodiment 23. The method of any one of embodiments 1-5, wherein the subject is canine.

VI. CONCLUSIONS

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes certain processes and compositions of matter, some of which embody the invention(s). Such descriptions or illustrations are not intended to limit the scope of what can be claimed, and are provided as aids in understanding the claims, enabling the making and use of what is claimed, and teaching the best mode of use of the invention(s). If this description and accompanying drawings are interpreted to disclose only a certain embodiment or embodiments, it shall not be construed to limit what can be claimed to that embodiment or embodiments. Any examples or embodiments of the invention described herein are not intended to indicate that what is claimed must be coextensive with such examples or embodiments. Where it is stated that the invention(s) or embodiments thereof achieve one or more objectives, it is not intended to limit what can be claimed to versions capable of achieving all such objectives. Any statements in this description criticizing the prior art are not intended to limit what is claimed to exclude any aspects of the prior art.

Additionally, the disclosure shows and describes certain embodiments of the processes, compositions of matter, and other teachings disclosed, but it is to be understood that the teachings of the present disclosure are capable of use in various other combinations, modifications, and environments and is capable of changes or modifications within the scope of the teachings as expressed herein.

Any section headings herein are provided only for consistency with the suggestions of 37 C.F.R. § 1.77 or otherwise to provide organizational queues. These headings shall not limit or characterize the invention(s) set forth herein.

I claim:

1. A method of supplementing collagen synthesis in a subject, the method comprising: administering a composition containing a manganese mineral topically or by inhalation to the subject while the subject is undergoing collagen therapy; wherein the composition is a suspension of the manganese mineral in water, administered by immersion of the subject in the composition.

2. The method of claim 1, wherein the manganese mineral contains $MnCO_3$.

3. The method of claim 1, wherein the manganese mineral is rhodochrosite.

4. The method of claim 1, wherein the manganese mineral is insoluble in water.

5. The method of claim 1, wherein the collagen therapy is orally administered as hydrolyzed collagen.

6. The method of claim 1, wherein the composition is a suspension of the manganese mineral in a fluid carrier.

7. The method of claim 1, wherein the composition is administered in the form of one or more of: a gel, a lotion, viscous water, and a hydrosol.

8. The method of claim 1, wherein the subject is suffering from one or more of: facial wrinkles, hair loss, eyelash thinning, slow nail growth, elastosis, joint pain, fatigue, Raynaud's syndrome, and fibromyalgia.

9. The method of claim 1, comprising administering the collagen therapy to the subject.

10. The method of claim 1, wherein the subject is human.

11. A method of supplementing collagen synthesis in a subject, the method comprising: administering a composition containing a manganese mineral topically or by inhalation to the subject while the subject is undergoing collagen therapy, wherein the subject is canine.

* * * * *